United States Patent [19]

Chakrabarti

[11] 4,223,009
[45] * Sep. 16, 1980

[54] HAIR PREPARATION CONTAINING VINYL PYRROLIDONE COPOLYMER

[75] Inventor: Paritosh M. Chakrabarti, Wayne, N.J.

[73] Assignee: GAF Corporation, New York, N.Y.

[ * ] Notice: The portion of the term of this patent subsequent to Aug. 21, 1996, has been disclaimed.

[21] Appl. No.: 805,397

[22] Filed: Jun. 10, 1977

[51] Int. Cl.² ........................ A61K 7/06; A61K 7/11
[52] U.S. Cl. ................................. 424/47; 8/127.51; 424/DIG. 1; 424/DIG. 2; 424/70; 424/71
[58] Field of Search ................... 424/DIG. 1, DIG. 2, 424/47, 70, 71; 8/127.51

[56] References Cited

U.S. PATENT DOCUMENTS

| | | | |
|---|---|---|---|
| 3,144,391 | 8/1964 | Goff | 424/47 X |
| 3,145,147 | 8/1964 | Glickman | 424/47 |
| 3,423,367 | 1/1969 | Merijan et al. | 424/47 X |
| 3,530,215 | 9/1970 | Grief et al. | 424/71 X |
| 3,910,862 | 10/1975 | Barabas et al. | 424/71 X |
| 3,914,403 | 10/1975 | Valan | 424/47 |
| 3,954,960 | 5/1976 | Valan | 424/47 |
| 3,980,769 | 9/1976 | Ghilardi et al. | 424/70 |
| 3,996,146 | 12/1976 | Tarasov et al. | 424/70X |
| 4,035,478 | 7/1977 | Mullen | 424/70 |

*Primary Examiner*—James O. Thomas, Jr.
*Assistant Examiner*—Vera C. Clarke
*Attorney, Agent, or Firm*—W. C. Kehm

[57] ABSTRACT

Hair preparations containing a copolymer of about 99.5 to 45.1 mole percent vinyl pyrrolidone and about 0.5 to 4.9 mole percent diloweralkylaminoalkyl acrylate or methacrylate, and method of setting and conditioning hair therewith.

17 Claims, No Drawings

HAIR PREPARATION CONTAINING VINYL PYRROLIDONE COPOLYMER

This invention relates generally to cosmetic preparations and especially to hair setting and conditioning compositions containing certain copolymers of vinyl pyrrolidone (N-vinyl-2-pyrrolidone), hereafter referred to as VP.

In the field of hair care, setting, waving, conditioning and the like, several broad types of hair treating preparations have been proposed, the principal ones being cationic surfactants, superfatting materials, water soluble proteins and synthetic polymers, in a suitable cosmetically acceptable medium. The synthetic polymer-containing preparations are generally regarded as most effective, particularly those containing water soluble cationic polymers which are substantive to hair and exhaust thereon from solution or diluent medium. British Pat. No. 1,331,819 and U.S. Pat. Nos. 3,910,862 and 3,954,960, the disclosures of which are incorporated herein for reasons which will become apparent, describe water soluble cationic quaternized copolymers of VP and a dialkylaminoalkyl acrylate or methacrylate, and hair care compositions containing such copolymers which have been found to be highly effective in providing most of the properties considered necessary in the theoretically perfect hair preparation, as in fact also described in said patents. The hair preparations described in said patents are however not optimal in certain respects, as for example cost of producing the quaternized copolymers, and a curl retention under high humidity conditions, an ease of removability and/or a resistance to build-up not as high as could be desired.

It is an object of this invention to provide hair treating compositions which will not be subject to one or more of the above disadvantages. Another object of the invention is the provision of such compositions containing lower-cost copolymers. Still another object of the invention is the provision of hair setting and conditioning compositions with improved curl retention under high humidity conditions, ease of removability, and/or resistance to build-up with repeated use. Yet a further object of the invention is the provision of an improved method of treating, setting and/or conditioning hair (human hair on or off the head as in wigs) with such compositions. Other objects and advantages will appear as the description proceeds.

The attainment of one or more of the above objects is made possible by this invention which includes the provision of:

A hair setting and conditioning composition comprising, approximately by weight, I. 0.1 to 35% of a film-forming copolymer having a molecular weight of about 15,000 to 1,500,000 and containing A. about 99.5 to 45.1 mole percent of units derived from vinyl pyrrolidone, B. about 0.5 to 4.9 mole percent of units derived from a monomer of the formula $$CH_2=CR^1-COOR^2-NR^3R^4$$

wherein
$R^1$ is H or $CH_3$,
$R^2$ is $C_{1-20}$ alkylene, and
$R^3$ and $R^4$ are independently $C_{1-4}$ alkyl, and C. 0 to about 50 mole percent of units derived from at least one ethylenically unsaturated copolymerable monomer different from A and B, II. 0.05 to 10% of at least one member of the group consisting of cosmetically acceptable organic surface active agents, thickening agents, plasticizers and sequestering agents, in III. a solvent base selected from the group consisting of water, monohydric $C_{2-3}$ aliphatic alcohols, 1,1,1-trichloroethane, methylene chloride, and mixtures thereof.

The above-mentioned U.S. patents disclose the production of quaternized derivatives of polymers containing the above-defined A, B and optional C units but with B present in proportions of at least 5 mole percent. The above-mentioned British Pat. No. 1,331,819 contains a similar disclosure but with B being present in proportions of 1 to 80 mole percent. It was highly surprising to discover that elimination of the quaternization step required in accordance with the teachings of said patents not only did not result in any significant detriment to the properties of the hair preparations containing such polymers, but proved advantageous in substantially reducing the costs of manufacture and in providing hair preparations yielding improved properties in the treated hair with respect to improved curl retention under high humidity conditions, ease of removability and/or resistance to build-up with repeated use, among other miscellaneous advantages.

It is to be noted that none of said patents discloses or contemplates hair preparations containing the non-quaternized precursors of the patented quaternized copolymers, and that British Pat. No. 1,331,819, though broadly suggesting copolymerization of VP with less than 5 mole percent (within the range of 1 to 80 mole percent) of monomer B, only discloses carrying out such copolymerization in ethanol and accordingly fails to disclose, even inherently, solutions of the non-quaternized copolymers (containing 0.5 to 4.9 mole percent of monomer B) in any non-ethanol medium.

It should accordingly be understood that the method of making the copolymers employed herein, by free radical addition polymerization, preferably in aqueous or alcoholic (e.g. ethanol, isopropanol) solution, and examples of the acrylate or methacrylate monomer B and of the optional ethylenically unsaturated (vinyl or vinylidene) monomer C employed in such method, are adequately disclosed in said patents, subject to the use of 0.5 to 4.9 mole percent of monomer B. As monomer B, di-$C_{1-2}$ alkyl-aminoethyl acrylates and methacrylates are preferred, especially dimethylaminoethyl methacrylate. Any of the other dialkylaminoalkyl acrylates and methacrylates disclosed in U.S. Pat. No. 3,910,862 at column 3, line 56 to column 4, line 15, may however be employed, in addition to their substantial equivalents in which the terminal dialkyl groups ($R^3$ and $R^4$) taken together form with the bonded N atom a 5 or 6 membered heterocyclic ring such as morpholino, methyl piperidino, pyrrolidino, and the like. Monomer B preferably constitutes about 1 to about 2.5, more preferably about 1.4, mole percent of the above-identified polymer I of the present invention. Correspondingly, polymer I preferably contains about 99 to about 97.5, more preferably about 98.6, mole percent of units derived from VP (monomer A).

Similarly, any of the monomers disclosed in British Pat. No. 1,331,819 at page 2, lines 65–82, may be employed to provide the optional ethylenically unsaturated copolymerizable monomer C units in said polymer I.

The copolymers employed according to the present invention can be prepared over a wide range of molecular weights, e.g. from about 15,000 to 1,500,000 or more, depending upon the particular choice of reactants, initiator, solvent and polymerizing conditions, lower temperatures being generally conductive to the formation of higher molecular weight copolymers. The desired molecular weight range in any particular instance will in general be influenced by the type, utility, and dispensing method of the cosmetic composition in which it will be employed. Since these copolymers are soluble in both water and alcohol, they can be employed in cosmetic compositions particularly hair preparations, containing an alcoholic, aqueous or mixed aqueous-alcoholic base or carrier. The preferred higher molecular weight copolymers of about 500,000 to 1,500,000 or more in addition act as their own thickeners, aqueous and/or alcoholic solutions displaying a slippery feel and facilitating application, local or overall, to the hair.

The above described copolymers of this invention can be employed in hair preparations and other cosmetic compositions in the same manner and with the same surface active agents, thickening agents, plasticizing agents and sequestering agents as the heretofore employed conventional film-forming resins, for example with the same additives and in the same formulations as disclosed for the quaternized copolymers in U.S. Pat. No. 3,954,960. They may generally be formulated for hair setting, waving, conditioning, coloring, and/or bleaching functions in the form of a lotion, cream (paste), gel, pump spray or pressurized aerosol. Conveniently, the copolymer is dissolved, preferably in proportions of about 0.5 to about 5% by weight of the formulation, in the solvent of choice, e.g. 1,1,1-trichloroethane, methylene chloride, or preferably ethanol, isopropanol, 2-methoxyethanol, or water or mixtures thereof, in the presence of (before, with, or after addition of) about 0.05 to about 10% by weight of one or a mixture of the known, conventional, cosmetically acceptable organic surface active agents, thickening agents, plasticizing agents and sequestering agents.

As cosmetically acceptable organic surface active agents useful in the cosmetic, particularly hair, preparations of this invention, any one or more of the anionic, ampholytic, polar nonionic, nonionic, zwitterionic and cationic organic surfactants disclosed in U.S. Pat. No. 3,489,686, at column 2, line 66 to column 5, line 2 may be employed.

As operative thickening agents there may be mentioned carboxymethycellulose, hydroxyethylcellulose, methylcellulose, magnesium aluminum silicate, Carbopols (B. F. Goodrich) such as Carbopol 940, and the like. Useful sequestering agents include sodium ethylenediaminetetracetates, polyphosphates, trisodium nitrilotriacetate and the like, corresponding K salts, etc.

As useful plasticizing agents (including emollients, lubricants), there may be mentioned lanolin and lanolin derivatives such as acetylated and ethoxylated lanolin alcohols and isopropyl lanolate, polyoxyethylenated sorbitan monooleate, trioleate and monostearate, ethylene, diethylene, propylene and hexylene glycols and their monomethyl and monoethyl ethers and monoacetates, glycerin, glycerol triacetate and monoricinoleate, long chain alcohols such as oleyl, isostearyl and cetyl alcohols and their polyoxyethylenated derivatives, e.g. with 2-30 moles of ethylene oxide, dimethyl, diethyl and dibutyl phthalates, triethylphosphate, isopropyl myristate and palmitate, dimethyl and methylphenyl polysiloxane and other silicones, and the like.

Certain volatile plasticizers may also be employed such as propionamide, benzoic and salicyclic acid, menthol, thymol, methyl-2-naphthylketone, hexachloroethane, benzophenone and acetamide.

Other optional conventional additives include opacifiers, colorants, perfumes, UV absorbers, preservatives, medicaments, suds boosters or depressants, penetrants, lustrants, deodorants, and the like.

In the above monomer B formula, $R^2$ may for example be methylene or preferably ethylene or may be branched or isomeric but preferably normal or linear hydroxyethylene, propylene, hydroxypropylene, butylene, pentylene, hexylene, heptylene, octylene, nonylene, decylene, dodecylene, tetradecylene, hexadecylene, octadecylene or di-decylene; and $R^3$ and $R^4$ may be independently butyl, t-butyl, isobutyl, propyl, isopropyl, ethyl, or preferably methyl.

The optional monomer C may be any conventional vinyl or vinylidene monomer other than B copolymerigable with A (VP). Exemplary of such monomers are the alkyl vinyl ethers, e.g. the methyl, ethyl, octyl and lauryl vinyl ethers; acrylic and methacrylic acid and esters thereof, e.g. methyl acrylate, ethyl acrylate and methyl methacrylate; vinyl aromatic monomers, e.g. styrene and alpha-methyl styrene; vinyl acetate and chloride; vinylidene chloride; acrylonitrile and methacrylonitrile and substituted derivatives thereof; acrylamide and methacrylamide and N-substituted derivatives thereof; crotonic acid and esters thereof, e.g. methyl and ethyl crotonate; and the like.

The compositions of this invention may be prepared and supplied in the form of concentrates containing up to 35% or more by weight of copolymer I in solution in water and/or alcohol.

The present invention includes a method comprising treating hair with an aqueous, alcoholic, or aqueous-alcoholic medium containing an effective amount of the above-defined copolymer I, such amount depending of course upon the desired function, e.g. conditioning, bodying, lusterizing, shape setting and holding, rinsing, protecting, improving manageability and the like, and generally ranging from about 0.1 to 5%, preferably about 0.2 to 2%, by weight in said medium. Such medium desirably also contains conventional hair preparation additives such as about 0.05 to about 10% of one or more of the above-mentioned cosmetically acceptable agents, i.e. surfactants, thickeners, plasticizers and sequestrants, in addition to other such conventional additives including those described elsewhere herein.

Because the copolymers employed herein, in contrast to those containing at least 5 mole percent of units from monomer B, have a relatively low substantivity to hair, the hair preparations containing them according to this invention are preferred for most left-on-the-hair uses such as setting and conditioning lotions, creams and gels, blow-dry conditioners and hair sprays of the pump or pressurized aerosol type. These copolymers are easily washed or shampooed out of the hair, thereby avoiding resin buildup which leads to reduced hair manageability and to an artifically coated appearance. The present compositions may if desired also be employed in rinse-type hair conditioners and as a conditioner in shampoos.

In general, for use in the form of a lotion, cream or gel for conditioning, bodying, lusterizing, shape setting and holding (curling, waving, straightening, shaping), improving manageability (combability, brushability, shaping), protection against mechanical and chemical influences, and the like, the invention involves the treatment of human hair with a lotion, cream or gel containing, approximately by weight, 0.1 to 5% of the above-defined polymer I in 99.9 to 95% of a solvent medium, 50 to 100% of which is water and 0 to about 50% of which is at least one $C_{2-3}$ aliphatic monohydric alcohol, desirably with 0.05 to 10% of said medium being replaced by at least one cosmetically acceptable organic surface active agent, thickening agent, plasticizing agent or sequestering agent. In most instances, the lotion, cream or gel composition contains about 0.05 to 1.0% of at least one surface active agent and 0.1 to 1.0% of a thickener.

For application in the form of a pump spray, about 3 to about 70% of said solvent medium is composed of said alcohol to facilitate the spray function and hasten drying.

For application as a conditioning rinse, said solvent medium is generally devoid of alcohol, desirably with about 0.05 to 10% of said medium being replaced by at least one of said cosmetically acceptable agents. In most instances the conditioning rinse contains about 1.5 to 10% of at least one surface-active agent and 0 to about 4% of at least one plasticizer, e.g. glycerolstearate.

For application as a conditioning shampoo, said solvent medium is also generally devoid of alcohol which acts as a foam or suds depressant, with about 10 to 50% of said medium being replaced by at least one surface active agent acting as detergent, and desirably with about 0.05 to 10% of said medium being replaced by at least one cosmetically acceptable thickener, plasticizer or sequestrant, especially the plasticizer, e.g. polyethylene glycol (6000) stearate and/or propylene glycol. One or a mixture of two or more of the surface active agents disclosed in U.S. Pat. No. 3,489,686, as indicated above, may function as the detergent component in the shampoo.

A pressurized aerosol formulation according to the invention may contain, approximately by weight, 0.1 to 5% of said copolymer I, 0 to 10% of one of the aforesaid agents, 25 to 60% of the aforesaid alcohol, 0 to 40% of water, and 10 to 70% of propellant.

In the above formulations, all or part of the alcohol may be replaced by 1,1,1-trichloroethane or methylene chloride or the like. Any propellant may be employed for pressurizing the aerosol in its valved pressure container, pressurized or liquified gas or the like. For example, where not prohibited, any of the known chlorofluoro hydrocarbons, or mixtures thereof, may be employed, if desired in admixture with other types of propellants such as described below. Freons 11, 12 and 114, particularly dual mixtures thereof, are useful, in addition to other Freons and their counterparts available as Genetrons, Isotrons, etc. Other useful propellants include any or a mixture of normal and isopropanes and butanes, nitrogen, nitrous oxide, carbon dioxide, and the like.

The VP copolymers employed herein have a number of important advantages relative to prior art hair setting and conditioning resins, including:
1. Complete water solubility under all pH conditions.
2. Amenability to yield clear aqueous, alcoholic, or aqueous-alcoholic liquid formulations.
3. Lower cost, particularly as compared with their quaternized derivatives.
4. Superior hair holding power under high humidity conditions.
5. Ready removeability by washing or shampooing.

The compositions of the present invention are particularly useful for the following distinctive on-hair performance criteria;
1. Good adhesion and spreading on hair.
2. Detangling of wet hair.
3. Provides hair with a lustrous "natural" as against a dirty "coated" appearance.
4. Adds body and a lively bounce to hair.

The copolymer I employed herein may, as indicated above, be prepared by the procedures disclosed in U.S. Pat. No. 3,910,862, omitting of course the final quaternizing step, e.g. Examples 1, 2, 4 and 6 of said patent, with suitable adjustment of the mole percent of monomer B to about 0.5 to 4.9. Another preferred method of preparing copolymer I is set forth in Example A below. All amounts and proportions referred to herein and in the appended claims are by weight unless otherwise indicated.

EXAMPLE A

| Materials | Amounts |
|---|---|
| Distilled Water | 1400 g. |
| Vinylpyrrolidone (VP) | 343 g. (330 ml.) |
| Dimethylaminoethyl methacrylate (DMAEMA) | 7.0 g. |
| Azobisisobutyronitrile (AIBN) | 0.6 g. |

Charge 1350 g. of the water and 310 ml. VP to a kettle equipped with mechanical stirrer, reflux condenser, thermometer and gas inlet tube and adjust to a pH of about 7 with citric acid or caustic soda solution. Purge with nitrogen and heat to 75° C. under nitrogen purge.

Mix the DMAEMA with the remaining 50 g. of water and similarly adjust to pH of about 7, dilute to 65 ml. with distilled water and charge to a dropping funnel.

Dissolve the AIBN in the remaining VP, add to kettle at 75° C. and hold for 5 minutes.

Add 35 ml. of the DMAEMA solution to the kettle over 10 minutes, followed by 20 ml. over 10 minutes and 15 ml. over 10 minutes. Hold at 75° C. for 1 hour, sample and analyze for VP monomer. Hold an additional 1.6 hours, cool and discharge.

The resulting product has a pH of about 6.5 to 6.7 and bulk Brookfield viscosities of 34,000–48,000 cps. using a #7 spindle at 20 rpm.

As also indicated above, the copolymer I of this invention may be substituted for the quaternized copolymers employed in the various formulations exemplified in U.S. Pat. No. 3,954,960, e.g. Examples 2–4 and 6–10. The following additional examples are only illustrative of further preferred embodiments of this invention and are not to be regarded as limitative. In these examples and in the appended claims, all amounts and proportions are by weight unless otherwise indicated; the VP/DMAEMA 98/2 of the present invention has a number average molecular weight (M.W.) ranging from about 700,000 to at least 1,000,000; the VP/DMAEMA 90/10 has a similar M.W.; the VP/DMAEMA 80/20 has a M.W. range of about 1,000,000 to 1,500,000; DMAEMA is dimethylaminoethyl methacrylate;

"Ethoquat" indicates quaternization with diethylsulfate, such quaternized derivatives having the same M.W. range as the non-quaternized precursors; PVP K90 (VP homopolymer) has a M.W. of about 360,000; and PVP K30 has a M.W. of about 40,000.

The following test procedure used for these examples was developed to determine on a comparison basis the hair-holding qualities of different products under varying temperature and humidity conditions:

Humidity Curl Retention Test

1. Human, untreated hair is used for this test.
2. A master shank of hair is subdivided into a series of individual swatches each nine inches long and weighing 1.5 grams.
3. A minimum of 6 swatches is used for each product to be evaluated.
4. In each case 1.2 ml. of the product is used per hair swatch. The product is worked down into the swatch so as to give a uniform application throughout the entire swatch.
5. Each swatch is combed twice immediately after product application. It is then curled using a ⅝" O.D. mandril and pinned.
6. The swatches are then thoroughly dried using a salon hair dryer at high temperature setting approximately 1½ hours.
7. The humidity chamber is preconditioned to the desired temperature and humidity.
8. After drying, the swatches are unpinned and carefully opened. Each swatch is individually mounted on a precalibrated plexiglass board. The initial length is recorded. The swatches are so spaced so no one cell will have an abnormal number of swatches in any one area of the humidity chamber.
9. The plexiglass boards are then placed in the humidity chamber. The temperature and relative humidity are recorded.
10. Swatch length readings are taken at various prescribed time intervals with the corresponding temperature and relative humidity recorded.
11. The data for each product obtained on the six or so swatches are averaged for comparison purposes.
12. Since the test is dependent upon the nature of hair used, cross comparison between two different lots of hairs is not meaningful.

The following examples illustrate the preferred left-on-the-hair type embodiments of this invention in addition to the less preferred rinse type conditioner and conditioning shampoo embodiments.

EXAMPLE 1

Two setting lotions are formulated using PVP-K-90 in one and copolymer Vinylpyrrolidone/Dimethylaminoethyl methacrylate (VP/DMAEMA=98/2) in the other. These two lotions are compared side by side using the test procedure described above. The relative curl retention at different intervals of time are shown below.

| Setting Lotion Formulation | Parts |
| --- | --- |
| Resin Solids | 1.5 |
| Isostearyl alcohol + 10E.O. | 0.08 |
| Silicone Fluid SF-1066 | 0.08 |
| Perfume | 0.10 |
| Ethanol | 32.90 |
| FDC Blue #1 (0.6% aq.) | 0.05 |
| Distilled Water | Q.S. to 100 |
| Citric Acid (10%) | Q.S. to pH 6.3 |

| | % Curl Retention, 90% RH, 80° F. | |
| --- | --- | --- |
| | Resin Solids VP/DMAEMA 98/2 | Resin Solids PVP K 90 |
| 0 minutes | 100 | 100 |
| 20 minutes | 92 | 50 |
| 30 minutes | 75 | 35 |
| 60 minutes | 33 | 20 |

*General Electric lubricant - dimethyl polyoxyalkylene ether polysiloxane copolymer.

The above data shows that at equal solids content the copolymer of the current invention (VP/DMAEMA 98/2) containing only 2 weight percent DMAEMA is significantly superior in curl retention under humid conditions than the polyvinylpyrrolidone homopolymer.

EXAMPLE 2

This example shows comparative curl retention values between PVP-K-30 and VP/DMAEMA (98/2) under identical conditions.

| | % Curl Retention. 2% Aqueous Solution of Product on Hair Swatches (80% RH and 80° F.) | | | |
| --- | --- | --- | --- | --- |
| | 0 min. | 30 min. | 60 min. | 90 min. |
| PVP K-30 | 100 | 34 | 8 | 4 |
| VP/DMAEMA (98/2) | 100 | 100 | 98 | 93 |

Once again outstandingly superior humidity holding characteristics in the copolymer of the current invention are shown.

EXAMPLE 3

This example is designed to show that the copolymers of the current invention do not leave any significant build-up on hair on repeated use and shampoo, whereas, prior art cationic quaternary resins leave a positive build-up on repeated use.

The following test procedure is used to demonstrate presence of the resin on hair:

A swatch (approximately 0.3 g.) of virgin light blonde hair is thoroughly washed with ethanol and dried. The dried hair swatch is placed in the test solution and held there for 3 minutes. The hair swatch is then rinsed with fresh water and while still damp dipped into a 0.5% aqueous solution of a special macromolecular polyanionic direct red azo dye (Direct Fast Red C.I. #32*) adjusted to pH 3.5 with sulfuric acid for 5 minutes at 40° C. The swatch is rinsed well with fresh water and visually examined for intensity of the red color it may have picked up. The intensity of the red color on the hair swatch indicates the degree of deposition of cationic resin onto the hair. Absence of red color on the swatch indicates lack of substantivity of the cationic resin.

*Erie Fast Rubine B Concentrate (Allied Chemical).

Theory: Hair in contact with water usually acquires a negative charge. However, when a cationic resin is deposited onto it, it becomes positively charged. The positively charged hair attracts the negatively charged macro polyanion of the red dye molecule and holds it tenaciously on to the surface of the hair. The hair swatch thus acquires a substantive red color. The intensity of the red color on the hair swatch is a function of the extent of adsorption of the dye, which in turn is a function of the cationic charge density on the hair, which again is a function of the extent of deposition and substantivity of the particular cationic resin on the hair.

The products are formulated in the setting lotion formulation of Example 1. The hair swatches are immersed into the setting lotions and tested according to the test procedure given above. The color development, which is a function of resin concentration on the hair, is noted in each case.

Another set of similar swatches is treated with the same setting lotions, shampooed and then tested by the color test for residual resin on the hair. The process is repeated on a third set which is treated with setting lotions, shampooed, treated with setting lotions again and shampooed again before checking for resin on the hair by the color test. The test is conducted up to 10 successive lotion applications and shampoos. The results are summarized in the following table.

| Product | First application. No Shampoo | Red Color Intensity on Swatch Number of application-shampoo cycles | | | |
|---|---|---|---|---|---|
| | | 1 | 3 | 5 | 10 |
| 98/2 VP/DMAEMA | 2–3 | 1 | 1 | 1 | 1 |
| 90/10 VP/DMAEMA-Ethoquat | 8 | 4 | — | — | 9 |
| 80/20 VP/DMAEMA-Ethoquat | 10 | 5 | 7 | 8 | 10 |
| Control (water only) | 1 | 1 | 1 | 1 | 1 |

The color intensities are rated in a scale of 1 to 10, 1 meaning almost neutral color (i.e. control with water) and 10 rather intense red indicating a high degree of resin on the hair.

The above results show that the 98/2 VP/DMAEMA copolymer does not have any tendency to build-up on hair upon repeated use-shampoo conditions whereas the prior art materials do definitely build-up upon repeated use-shampoo conditions.

EXAMPLE 4

| Wave Setting Gel | Parts |
|---|---|
| Carbopol 940* | 0.75 |
| Uvinul MS-40** | 0.10 |
| Ethylenediaminetetraacetic acid disodium salt (0.1% aq.) | 0.10 |
| Triethanolamine | 1.00 |
| Water, distilled | 96.55 |
| VP/DMAEMA 98/2 (100% solids) | 1.50 |
| Color F.D.C. Yellow #5 (0.6%) | 0.3 |
| Fragrance | 0.1 |
| Preservative | 0.1 |

*B.F. Goodrich Chemical thickener - water soluble polymer of acrylic acid crosslinked with under 2% of a polyallylether of sucrose having an average of about 5–6 allyl groups per sucrose molecule.
**GAF Corporation UV absorber - 2-OH-4-methoxybenzophenone-5-sulfonic acid.

EXAMPLE 5

| Wave Setting Gel | Parts |
|---|---|
| Carbopol 940 | 0.35 |
| Uvinul MS-40 | 0.10 |
| Ethylenediaminetetraacetic acid, disodium salt (0.1% aq.) | 0.10 |
| Triethanolamine | 0.50 |
| Water, distilled | 97.05 |
| VP/DMAEMA 98/2 (100% solids) | 1.50 |
| Opacifier* | 0.40 |
| Color F.D.C. Yellow #5 (0.6%) | 0.3 |
| Fragrance | 0.1 |
| Preservative | 0.1 |

*GAF Corporation - 70% styrene graft polymerized on 30% PVP.

EXAMPLE 6

| Pump Spray Conditioner (for Blow Drying) or Hair Spray (for Regular Use) | Parts |
|---|---|
| VP/DMAEMA 98/2 (100% solids) | 1.00 |
| Ammonyx 4002* | 0.40 |
| Tween 20** | 0.20 |
| Fragrance | 0.1 |
| Ethanol | 60.00 |
| Water, distilled | 38.40 |

*Onyx Chemical - stearyl dimethyl benzyl ammonium chloride (100%).
**I.C.I. - Polyoxyethylene (20) sorbitan monolaurate

EXAMPLE 7

| Pump-Type Blow Dry Hair Conditioner | Parts |
|---|---|
| VP/DMAEMA 98/2 | 1.00 |
| Ammonyx KP* | 0.60 |
| Tween 20 | 0.20 |
| Perfume | 0.10 |
| Ethanol | 3.00 |
| Distilled Water | Q.S. to 100 |

*Onyx Chemical - oleyl dimethyl benzyl ammonium chloride.

EXAMPLE 8

| Conditioning Shampoo | Parts |
|---|---|
| Miranol C2M* | 15.0–20.00 |
| Coconut diethanolamide | 4.0 |
| Propylene glycol | 7.0 |
| VP/DMAEMA 98/2 | 1.5 |
| PEG 6000 distearate** | 5.0 |
| Dinonyl phenol 30 150 E.O. | 5.0 |
| Water, distilled | Q.S. to 100 |

*Coconut imidazolinium-N-ethoxymethylcarboxy-N-acetic acid, disodium salt - Miranol Corporation.
**Armak - polyethylene glycol (6,000 M.W.) distearate.

EXAMPLE 9

| Conditioning Shampoo | Parts |
|---|---|
| Sipon LT6* | 35.0 |
| Coconut diethanolamide | 4.0 |
| Ceraphyl 65** | 2.5 |
| VP/DMAEMA 98/2 | 0.5 |
| Perfume | 0.1 |

| Conditioning Shampoo | |
|---|---|
| | Parts |
| Distilled water | Q.S. to 100 |

*Alcolac Chemical - triethanolamine lauryl sulfate
**Van Dyke Company - mink oil-amidopropyl dimethyl 2-hydroxyethyl ammonium chloride.

EXAMPLE 10

| Blow Dry Conditioner | |
|---|---|
| | Parts |
| VP/DMAEMA 98/2 | 1.00 |
| Carbopol 940 (100% solids) | 0.10 |
| Triethanolamine | 0.15 |
| Isostearyl alcohol + 10 E.O. | 0.05 |
| Tween 20 | 0.13 |
| Perfume | 0.20 |
| F.D.C. Yellow #5, (0.6% aq.) | 0.07 |
| Ethanol | 44.82 |
| Water, distilled | Q.S. to 100 |

EXAMPLE 11

| Cream Rinse | |
|---|---|
| | Parts |
| Arquad 2 HT-75* | 7.5 |
| Glyceryl monostearate | 2.0 |
| VP/DMAEMA 98/2 | 0.4 |
| Distilled water | 90.0 |
| Glutaraldehyde | 0.1 |
| Citric Acid | Q.S. to pH 5.0–5.5 |

*Armak - cationic dimethyl di (hydrogenated tallow) ammonium chloride, 75% active.

EXAMPLE 12

| Cream Rinse | |
|---|---|
| | Parts |
| Triton X400* | 7.0 |
| Glyceryl monostearate | 2.0 |
| Ceraphyl 28** | 1.0 |
| VP/DMAEMA 98/2 | 0.5 |
| Distilled water | 90.0 |
| Glutaraldehyde | 0.4 |
| Sodium hydroxide | Q.S. to pH 5.0–5.5 |

*Rohm and Haas - cationic stearyl dimethyl benzyl ammonium chloride, 25% solids.
**Van Dyke - cetyl lactate.

EXAMPLE 13

| Clean Creme Rinse | |
|---|---|
| | Parts |
| VP/DMAEMA 98/2 | 0.2 |
| Ammonyx KP* | 4.0 |
| Natrosol HHR** | 0.4 |
| Distilled water | 95.4 |

*Onyx Chemical - cationic oleyl dimethyl benzyl ammonium chloride.
**Hercules - hydroxyethyl cellulose.

EXAMPLE 14

| Aerosol Hair Spray | |
|---|---|
| | Parts |
| VP/DMAEMA 98/2 | 2.0 |
| Ethanol | 50.0 |
| Propellants | |
| Isobutane | 13.5 |
| Propane | 1.5 |
| Distilled water | Q.S. to 100 |

EXAMPLE 15

| Setting Lotion Concentrate | |
|---|---|
| | Parts |
| VP/DMAEMA 98/2 | 8.0 |
| PVP/VA E 735* | 37.0 |
| Ammonyx KP | 2.4 |
| Tween 20 | 1.2 |
| Distilled water | Q.S. to 100 |

*GAF Corporation - 70 VP/30 Vinyl acetate copolymer, 50% in alcohol.

For use, dilute 1 part with 7 parts water.

This invention has been disclosed with respect to certain preferred embodiments and it will be understood that modifications and variations thereof obvious to those skilled in the art are to be included within the spirit and purview of this application and the scope of the appended claims.

What is claimed is:

1. A hair setting and conditioning composition comprising, approximately by weight,
I. 0.1 to 35% of a film-forming copolymer having a molecular weight of about 15,000 to 1,500,000 and containing
A. about 99.5 to 45.1 mole percent of units derived from vinyl pyrrolidone,
B. 0.5 to 4.9 mole percent of units derived from a monomer of the formula $$CH_2=CR^1-COOR^2-NR^3R^4$$

wherein
$R^1$ is H or $CH_3$,
$R^2$ is $C_{1-20}$ alkylene, and
$R^3$ and $R^4$ are independently $C_{1-4}$ alkyl, and
C. 0 to about 50 mole percent of units derived from at least one ethylenically unsaturated copolymerizable monomer different from A and B,
II. 0.05 to 10% of at least one member selected from the group consisting of cosmetically acceptable organic surface active agents, thickening agents, plasticizers and sequestering agents, in
III. a solvent base selected from the group consisting of water, monohydric $C_{2-3}$ aliphatic alcohols, 1,1,1-trichloroethane, methylene chloride, and mixtures thereof.

2. A pressurized aerosol hair spray containing about 10 to 70% of a propellant and a hair setting or conditioning amount of a composition as defined in claim 1.

3. A pressurized aerosol hair spray as defined in claim 2 wherein copolymer I consists essentially of units derived from vinyl pyrrolidone and dimethylaminoethyl methacrylate.

4. A hair conditioning shampoo containing, approximately by weight, 10 to 50% of at least one organic anionic, cationic, nonionic or amphoteric detergent and a conditioning amount of a composition as defined in claim 1.

5. A hair shampoo as defined in claim 4 wherein copolymer I consists essentially of units derived from vinyl pyrrolidone and dimethylaminoethyl methacrylate.

6. A composition as defined in claim 1 wherein polymer I consists essentially of units derived from vinyl pyrrolidone and dimethylaminoethyl methacrylate.

7. The composition of claim 1 containing 0 to 10% of at least one member II, and water as solvent base III.

8. A method for setting or conditioning hair comprising applying to the hair an effective amount of a composition as defined in claim 1.

9. A method for setting or conditioning hair comprising applying to the hair an effective amount of a composition as defined in claim 2.

10. A method for setting or conditioning hair comprising applying to the hair an effective amount of a composition as defined in claim 3.

11. A method for setting or conditioning hair comprising shampooing the hair with an effective amount of a composition as defined in claim 4.

12. A method for setting or conditioning hair comprising shampooing the hair with an effective amount of a composition as defined in claim 5.

13. A method for setting or conditioning hair comprising applying to the hair an effective amount of a composition as defined in claim 6.

14. A method for setting or conditioning hair comprising applying to the hair an effective amount of a composition as defined in claim 7.

15. A method for setting or conditioning hair comprising applying to the hair an aqueous, alcoholic, or aqueous-alcoholic medium containing an effective hair setting or conditioning amount of a film-forming copolymer having a molecular weight of about 15,000 to 1,500,000 and containing:

A. about 95 to 45.1 mole percent of units derived from vinyl pyrrolidone,

B. 0.5 to 4.9 mole percent of units derived from a monomer of the formula $$CH_2=CR^1-COOR^2-NR^3R^4$$

wherein
$R^1$ is H or $CH_3$,
$R^2$ is $C_{1-20}$ alkylene, and
$R^3$ and $R^4$ are independently $C_{1-4}$ alkyl, and C. 0 to about 50 mole percent of units derived from at least one ethylenically unsaturated copolymerizable monomer different from A and B.

16. A method as defined in claim 15 wherein copolymer I consists essentially of units derived from vinyl pyrrolidone and dimethylaminoethyl methacrylate.

17. A method as defined in claim 15 wherein said medium contains about 0.5 to 5% by weight of said copolymer.

* * * * *